United States Patent [19]

Ahmed

[11] Patent Number: 4,655,700
[45] Date of Patent: Apr. 7, 1987

[54] APPARATUS FOR IMPREGNATION OF POROUS SAMPLES FOR MATERIALS EVALUATION

[75] Inventor: Wase U. Ahmed, Roselle, Ill.
[73] Assignee: Buehler Ltd., Lake Bluff, Ill.
[21] Appl. No.: 439,996
[22] Filed: Nov. 8, 1982
[51] Int. Cl.$^4$ .................. B29C 39/04; B29C 39/42
[52] U.S. Cl. ........................................ 425/73; 141/5; 141/59; 141/129; 141/284; 222/166; 264/102; 264/DIG. 78; 425/117; 425/173; 425/261; 425/447
[58] Field of Search .................. 118/50; 427/294, 295; 264/101, 102, DIG. 78; 425/405 R, DIG. 60, 73, 75, 117, 173, 261, 447; 222/166, 357; 141/284, 5, 59, 129; 83/915.5

[56] References Cited

U.S. PATENT DOCUMENTS

| | | | |
|---|---|---|---|
| 2,463,550 | 3/1949 | Myerson et al. | 264/101 |
| 3,081,492 | 3/1963 | Grzegorczyk | 264/DIG. 78 |
| 3,413,391 | 11/1968 | Carroll et al. | 264/102 |
| 3,621,904 | 11/1971 | Fahlbusch | 222/166 |
| 3,664,786 | 5/1972 | Devine | 264/101 |

Primary Examiner—Jay H. Woo
Assistant Examiner—James C. Housel
Attorney, Agent, or Firm—Charles F. Pigott, Jr.

[57] ABSTRACT

An apparatus for impregnating porous samples for materials evaluation with an inert material which fills the pores of the samples. A plurality of samples are placed in mold cups on a rotatable table within a vacuum chamber, and a supply of impregnant or encapsulant material such as an epoxy resin is provided in a container mounted on a tiltable platform located above the rotatable table. A plurality of samples are thus mounted in respective molding cups spaced in a circle on the rotatable table, a supply of encapsulant material is provided in a cup placed in a cup holder on the tiltable platform, a vacuum is created within the chamber, and the table is intermittently rotated to position each molding cup with its sample in line with the tilt axis of the tiltable platform to permit tilting of the encapsulant cup to pour a supply of resin into the molding cup. The foregoing procedure is repeated until each of the molding cups has received a desired supply of the resin material, while the vacuum is maintained within the chamber.

5 Claims, 4 Drawing Figures

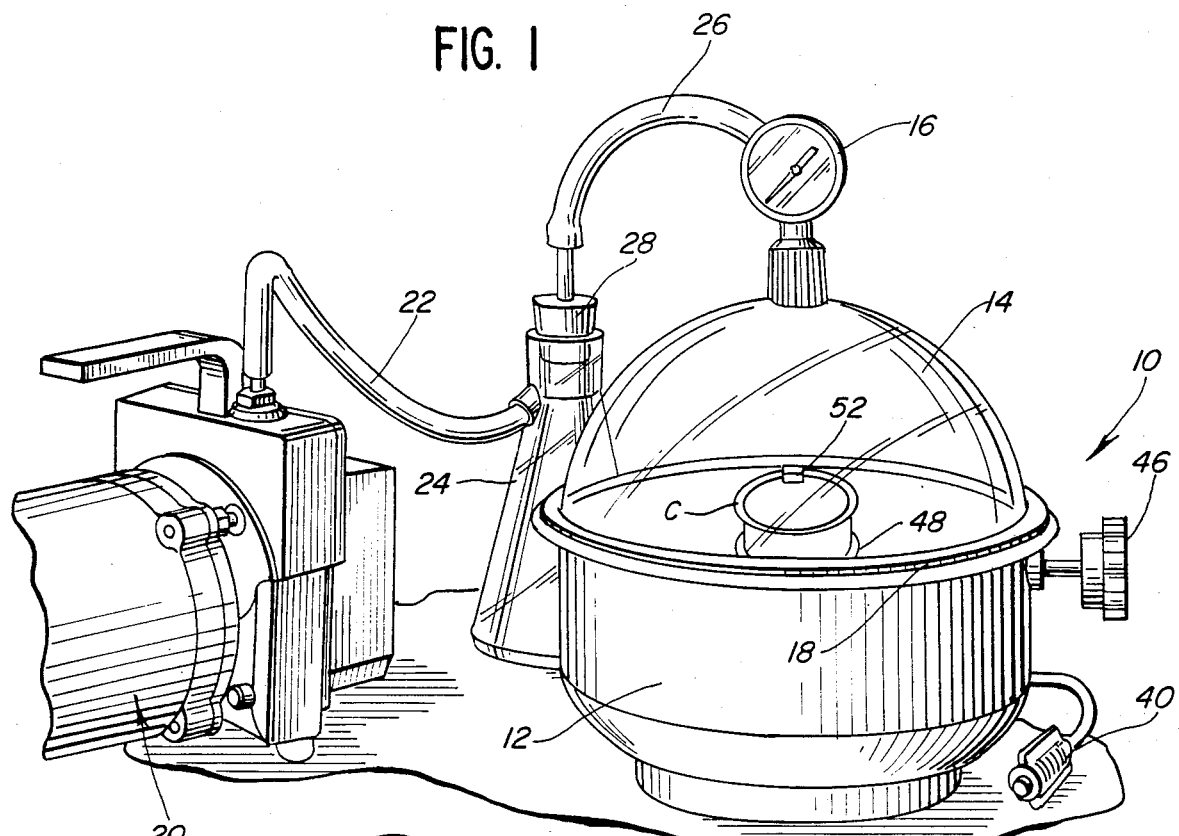
FIG. 1
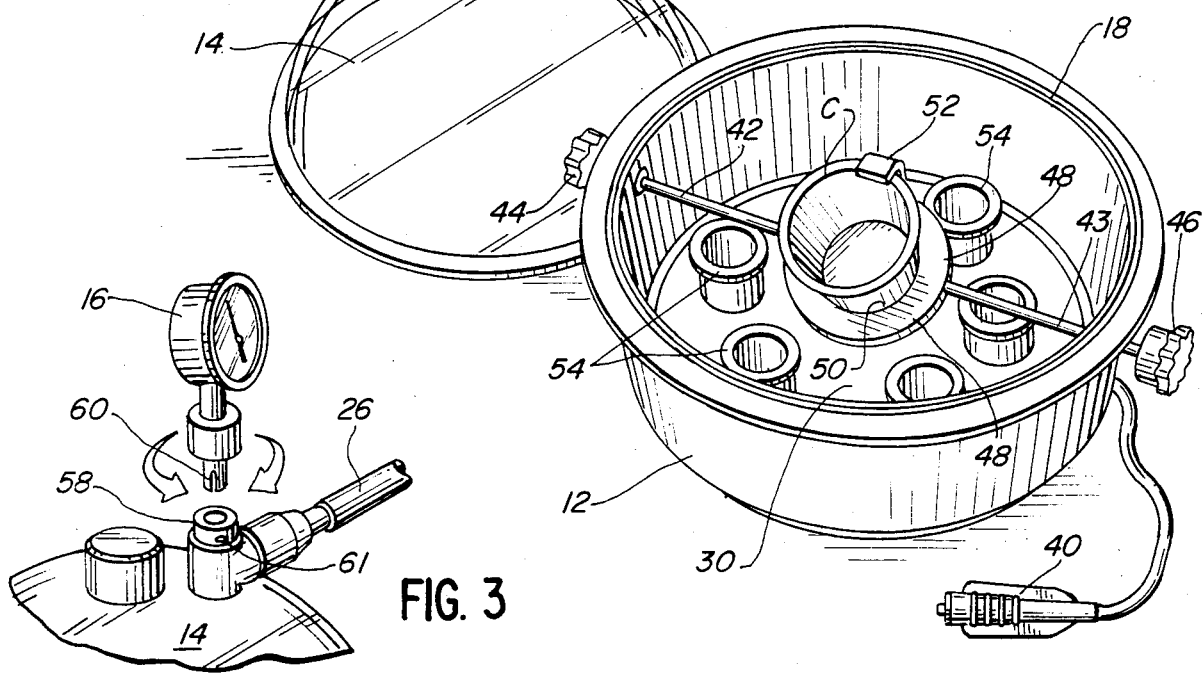
FIG. 2
FIG. 3

APPARATUS FOR IMPREGNATION OF POROUS SAMPLES FOR MATERIALS EVALUATION

BRIEF SUMMARY OF THE INVENTION

When it is desired to conduct microscopic examination of certain types of porous materials including various minerals, ceramics and metal alloys, such porous materials must be impregnated with an inert material which completely fills the pores in order to obtain a suitable surface for microscopic examination. Such an impregnated surface may then be subjected to the required abrasive grinding and polishing without causing degradation of the surface of the sample. If such porous samples are not impregnated prior to the grinding and polishing operations, it is likely the abrasives which are used to polish the surface will also cause a collapse of pore walls and degradation of the surface.

It is known to vacuum impregnate porous samples with an inert material to prevent collapse of the pore walls and eliminate sites where polishing debris may be entrapped, so that the pore structure which is observed during microscopic examination is the true structure from which accurate data may be obtained. However, known equipment for effecting vacuum impregnation is subject to certain significant disadvantages. Such equipment is slow and cumbersome because it is designed to impregnate only one sample after creation of a vacuum in a vacuum chamber, and therefore each sample impregnation requires creation of a separate vacuum.

In addition, the known method of impregnation involves admission of the encapsulant resin material to the chamber after creation of a vacuum by passing the resin through plastic and glass tubes from outside the chamber. The known procedure then involves shutting off the supply of resin and admitting air to the chamber through the resin tube. Such procedure often results in splattering and spilling, and the plastic and glass tubing must be solvent cleaned which is quite difficult.

It is an object of the present invention to provide a method and apparatus for vacuum impregnation of porous samples which permits impregnation of a plurality of samples with only a single pump-down operation to produce a vacuum.

Another object of the invention is to provide a method as above-described which is rapid and efficient, and which eliminates spilling and other clean-up problems.

A further one of my objects is to provide a method and apparatus for vacuum impregnation which permits the encapsulant resin material to be contained within the vacuum chamber prior to production of a vacuum, thereby eliminating the need for resin entry tubes and the like.

A more specific object of my invention is to provide a motor driven rotatable table within a vacuum chamber for the purpose of supporting a plurality of molding cups arranged in a circle on the table, each molding cup containing a porous sample to be impregnated, and to provide a tiltable platform above the table including a cup holder for holding a cup of resin from which controlled amounts of resin may be poured into the molding cups as the latter are positioned seriatim beneath the resin cup by intermittent rotation of the table.

The foregoing and other objects and advantages of the invention will be apparent from the following description of a preferred embodiment, taken in conjunction with the accompanying drawings.

DESCRIPTION OF THE DRAWINGS

FIG. 1 is a fragmentary perspective view of vacuum impregnation apparatus constructed in accordance with the present invention, including a vacuum chamber and an attached vacuum pump;

FIG. 2 is a perspective view of the vacuum chamber and interior components, showing the upper half of the chamber removed to better illustrate the interior components;

FIG. 3 is a fragmentary perspective view of a vacuum gauge mounted in the dome or lid of the vacuum chamber.

Figure 4:
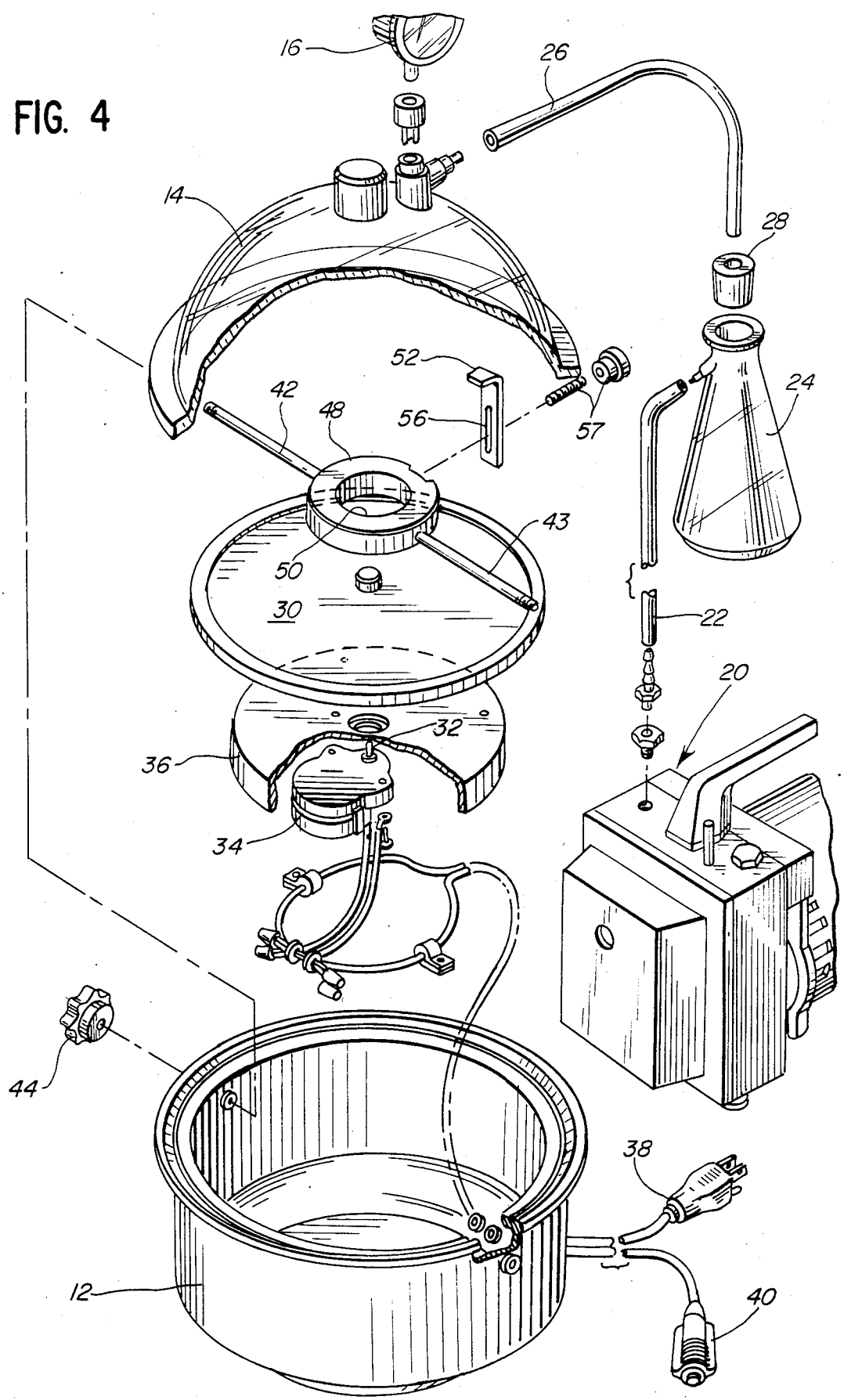
FIG. 4 is an exploded, perspective view showing the components of the vacuum impregnation apparatus of FIG. 1.

Now, in order to acquaint those skilled in the art with the manner of making and using my invention, I shall describe, in conjunction with the accompanying drawings, a preferred embodiment of the invention.

DETAILED DESCRIPTION OF THE INVENTION

Referring now to the drawings, a vacuum chamber 10 comprises a chamber base 12 and a transparent lid or dome 14 which incorporates a vacuum gauge 16. An O-ring seal 18 is provided around the lip of the chamber base 12 to facilitate creation of a vacuum within the chamber. A vacuum pump 20 is connected through vacuum hose 22 to a filtering flask 24, and a further vacuum hose 26 is connected from a rubber stopper 28 in the top of flask 24 to the transparent lid 14, whereby operation of pump 20 creates a desired vacuum within chamber 10.

FIGS. 2 and 4 show a round turntable 30 rotatably mounted in the bottom portion of base 12 to be driven from a drive shaft 32 of a synchronous gear motor 34 designed to rotate the turntable at 1.0 rpm. A motor support bracket is shown at 36 in FIG. 4. There are also shown an electrical cord 38 for connecting the drive motor 34 to a source of power, and a button control switch 40 for controlling motor 34. The button control switch 40 permits an operator to start and stop rotation of table 30 as desired.

The chamber base 12 is further provided with a tiltable cup holder assembly comprising a pair of shafts 42 and 43 which extend diametrically across the upper portion of base 12 and have their opposite ends projecting out of base 12 to mount control knobs 44 and 46. At the inner ends of shafts 42 and 43, there is mounted an annular platform or cup support 48 designed to permit the lower end of a tapered cup C to pass through a central opening 50 and seat within the annular support as shown in FIG. 2. The cup holder includes an adjustable stop 52 which serves to retain an upper rim portion of a cup seated in support 48 and retain the cup therein. The shafts 42 and 43 are capable of rotation about their common axis together with the annular cup support 48 for the purpose of pouring material from a cup C positioned in the support.

The operation of the foregoing apparatus will now be described. A plurality of specimen cups or molds 54 are arranged in a circle on turntable 30 as shown in FIG. 2, so the molds 54 will be positioned to receive encapsulant material poured from cup C. A specimen to be impregnated is placed in each of the molds or cups 54.

In addition, a quantity of encapsulant material is mixed and placed in a cup C which is then placed in cup holder 48. Cup stop 52 has a slot 56 and holding screw 57 (see FIG. 4) so the stop may be adjusted vertically relative to holder 48 and tightened to assure that cup C does not slip out of the holder 48 when tilted.

The clear plastic dome or lid 14 is then positioned on the base 12 of vacuum chamber 10. Vacuum gauge 16 is inserted into a vacuum port of a plastic tee 58 (see FIG. 3), and the gauge is turned so a relief slit 60 is out of alignment with an atmosphere hole 61 in the tee. The pump 20 is then started, and when the gauge reads 28 inches of mercury, the pump may be turned off. If necessary, table 30 is rotated through operation of button control switch 40 to locate the first sample cup or mold 54 in position to receive resin encapsulant material. The table 30 is then stopped, and through operation of manual knobs 44 and/or 46, cup C is tilted to pour a desired amount of resin into a mold 54.

It is preferred that the molds 54 should not be filled more than half full to prevent the resin encapsulant material from spilling under vacuum. The remaining space can be filled after the chamber 10 is opened to atmospheric pressure. After pouring the desired amount of resin into a mold 54, cup C may be tilted back to an upright position, and the control switch 40 operated to advance the next mold 54 into position, and the pouring process is then repeated. Such steps are repeated until each of the molds 54 has been supplied with a desired amount of resin encapsulant material.

After all the specimens have been encapsulated, the operator may slowly rotate the base of vacuum gauge 16 so relief slit 60 aligns with atmospheric hole 61, thereby allowing slow bleeding of air into vacuum chamber 10. It is preferred gauge 16 not be completely removed from dome 14, since a sudden rush of air into the chamber 10 could cause the encapsulant to spill or splatter. After the bleeding of air into the chamber 10, the dome 14 may be removed, additional encapsulant material may be added to each mold 54 as desired, and the mounts are allowed to cure.

The foregoing method and apparatus has the advantage that as many as 12 samples may be impregnated in only slightly more time than required to do one sample using the previously known method and apparatus. All such samples may be impregnated with only one pump-down operation to produce the required vacuum, and entry tubes to chamber 10 are eliminated because the resin material is contained within the chamber before the vacuum is created. The difficult clean-up operations normally required with other methods are eliminated.

What is claimed is:

1. Apparatus for vacuum impregnation of porous samples for the purpose of materials evaluation, said apparatus including a vacuum chamber with a base and a removable lid, and a pump for producing a vacuum in the chamber, the improvement comprising apparatus to permit both a plurality of samples and also a supply of impregnating material to be positioned within said vacuum chamber before a vacuum is created therein, said apparatus including, in combination, movable support means in said chamber for supporting a plurality of sample cups containing respective samples to be impregnated, drive means for intermittently moving said support means to a predetermined position, impregnation material container means located within said chamber above said movable support means for pouring a controlled amount of impregnating material to a sample cup positioned below on said support means, said container means comprising a container support tiltably mounted in said chamber above said support means, and control means external to said chamber for controlling the pouring of impregnation material from said container means to said sample cups seriatim, said control means comprising means for tilting said container support to pour encapsulant material from a container mounted on said container support, whereby through intermittent operation of said drive means a plurality of sample cups on said support means may be positioned seriatim beneath said container means to permit use of said control means to pour a controlled amount of impregnation material into said plurality of sample cups to impregnate said samples.

2. Apparatus of the type defined in claim 1 where said movable support means comprises a rotatable turntable on which a plurality of sample cups may be arranged for movement seriatim beneath said container means through intermittent operation of said drive means.

3. Apparatus for vacuum impregnation of porous samples for the purpose of materials evaluation, said apparatus being of the type including a vacuum chamber with a base and removable lid, and a pump for producing a vacuum in the chamber, the improvement comprising, in combination, rotatable turntable means in said chamber for supporting a plurality of sample cups containing respective samples to be impregnated, drive means for intermittently rotating said turntable, container support means tiltably mounted in said chamber above said turntable means for supporting a container of impregnating encapsulant material, and control means external to said chamber for tilting said container support means to pour encapsulant material from a container mounted on said container support means, whereby through intermittent operation of said drive means a plurality of sample cups on said turntable means may be positioned seriatim beneath said container support means to permit use of said control means to pour a controlled amount of encapsulant material into said plurality of sample cups to impregnate said samples.

4. Apparatus of the type defined in claim 3 where said container support means comprises a container support mounted on a generally horizontal rod which is rotatable about its own axis to tilt a container on said container support means to pour encapsulant material therefrom, and said control means comprises means attached to said rod for rotating the same from outside said chamber.

5. Apparatus of the type defined in claim 3 where said apparatus includes a vacuum base in which said turntable and container support means are mounted, and a removable transparent lid.

* * * * *